United States Patent
Mucko et al.

(10) Patent No.: US 6,905,499 B1
(45) Date of Patent: Jun. 14, 2005

(54) HEAT PIPE FOR CAUTERY SURGICAL INSTRUMENT

(75) Inventors: David Joseph Mucko, Lancaster, PA (US); Walter John Bilski, Mohnton, PA (US)

(73) Assignee: Thermal Corp., Stanton, DE (US)

( * ) Notice: Subject to any disclaimer, the term of this patent is extended or adjusted under 35 U.S.C. 154(b) by 311 days.

(21) Appl. No.: 10/305,608

(22) Filed: Nov. 26, 2002

(51) Int. Cl.⁷ .................................................. A61B 18/18
(52) U.S. Cl. ................................... 606/52; 606/45
(58) Field of Search ..................... 606/27–52

(56) References Cited

U.S. PATENT DOCUMENTS

| | | | |
|---|---|---|---|
| 4,474,170 A | * | 10/1984 | McConnell et al. ......... 126/636 |
| 4,492,231 A | | 1/1985 | Auth |
| 5,417,686 A | | 5/1995 | Peterson et al. |
| 5,437,662 A | | 8/1995 | Nardella |
| 5,443,463 A | | 8/1995 | Stern et al. |
| 4,785,807 A | | 7/1996 | Blanch |
| 5,647,871 A | * | 7/1997 | Levine et al. .................. 606/45 |
| 5,908,418 A | | 6/1999 | Dority et al. |
| 6,074,389 A | | 6/2000 | Levine et al. |
| 6,206,876 B1 | | 3/2001 | Levine et al. |
| 6,235,027 B1 | | 5/2001 | Herzon |
| 6,352,533 B1 | | 3/2002 | Ellman et al. |

* cited by examiner

*Primary Examiner*—Michael Peffley
*Assistant Examiner*—Pete Vrettakos
(74) *Attorney, Agent, or Firm*—Duane Morris LLP

(57) ABSTRACT

A heat pipe for a cautery surgical instrument such as a surgical forceps including a pair of elongate arms joined at an end so as to provide for resilient compressible movement of the arms between a normally open position and a squeezed closed position. The heat pipe provides for conduction of heat away from an electrode tip, and comprises an evaporator portion having a first diameter and a condenser portion spaced away from the evaporator end, and that transitions from the first diameter to at least one smaller diameter section. A socket is disposed within each arm of the forceps, and includes a longitudinal blind hole that is sized so as to releasably receive the smaller diameter section of the condenser portion, and a catch for engaging a portion of the arm.

7 Claims, 7 Drawing Sheets

HEAT PIPE FOR CAUTERY SURGICAL INSTRUMENT

FIELD OF THE INVENTION

The present invention generally relates to medical devices and, more particularly, to improved temperature control mechanisms for cautery devices using heat pipes.

BACKGROUND OF THE INVENTION

Medical treatments today often require that areas of organic tissue be cauterized or coagulated quickly, efficiently, and safely during the course of a surgical procedure. For example, surface tissue on a highly vascularized organ such as the human liver or brain may be cauterized immediately following the making of a surgical incision in order to prevent excessive bleeding. Alternatively, retinal tissue in a human eye may be photocoagulated during opthalmic surgery to correct injury or, skin tissue on a human scalp may be coagulated during hair transplant surgery to prevent bleeding resulting from graft incisions. Many prior art devices have been developed to perform cauterization or coagulation as appropriate for such varied applications. Known devices range from simple direct-contact cauteries, employing a heated wire element to burn or sear relatively large areas of tissue, to more complex laser photocoagulators using highly coherent, monochromatic laser light to perform pin-point coagulation of delicate tissue.

Typically, electrical energy is applied to the tissue being treated so as to cause local heating of the tissue. By varying the power output and the type of electrical energy, it is possible to control the extent of heating and thus the resulting surgical effect. Electrosurgery is often accomplished through the delivery of radio-frequency (RF) current through body tissue to raise the tissue temperature for cutting, coagulating, and desiccating. RF energy in the range of about 500 kilohertz to 1 megahertz, with about 30-watt to 40-watt power levels is typical of electrosurgical generators.

While tissue heating is the mechanism by which the various cautery surgical treatments are effected, it can also cause nonefficacious effects. Total body temperatures above 41.8° C. (107.2° F.) are detrimental to the functions of the central nervous system, heart, brain, liver, and kidneys, and may even cause histologically obvious damage to tissue cells, whereas, e.g., tumorcidal effects are generally not observed below 42.5. degree. C. (108.5° F.). At brain temperatures of over 41.8° C. (107.2° F.), the mechanism that regulates body temperature can become incapacitated, and there is danger of 'malignant' or 'runaway'hyperthermia. Further, temperatures of up to 45° C. (113.0° F.) may cause soft tissue necroses and fistulas as well as skin burns. Therefore, accurate temperature control of a localized area is critical to successful cauterization.

As a consequence, surgeons often operate prior electrosurgical devices at a very low power level. This prevents the electrode and the adjacent tissue from becoming too hot, too fast. Unfortunately, it also requires the surgeon to perform the procedure much more slowly than he would if he could operate the device at full power. As a result, the procedure takes much longer, requiring more operating room time.

It has been recognized that cooling the surgical site during electrosurgery is desirable. Several prior art systems have been developed which flush the surgical site with fluid during surgery or transfer the excess heat quickly away from the surgical site. One known apparatus which is used to remove heat from a surgical environment is a "heat pipe".

A heat pipe is an elongated tube having a wick running through its length with one end of the tube being in the hot environment and the other end being in a cooler or cold environment. The tube is charged with a selected amount of liquid, known as a "working fluid," having a particular boiling point such that the liquid will boil in the hot environment and give off vapors which will travel through the tube into the colder environment. In the colder environment the vapors condense back into liquid form and give up thermal energy through the latent heat of condensation. The condensed liquid is then soaked up by the wick and transferred through the wick by capillary action back to the hotter environment where the evaporating cycle is repeated. Such heat pipes can be very efficient so long as there is a difference in temperature between the hot environment and the cool environment.

For example, in U.S. Pat. Nos. 5,647,871, 6,074,389, and 6,206,876, issued to Levine et al., an electrosurgical device, system and a method of electrosurgery are disclosed in which electrosurgical electrodes are cooled by a heat pipe. The device includes at least one electrode for applying the required electrical energy to tissue at a surgical site. During surgery, an internal cavity within the electrode forms a heat pipe heat transfer device. The electrode is closed at both its proximal and distal ends. The cavity within each electrode is evacuated and contains a working fluid, e.g., water. When the distal end of an electrode contacts tissue heated by the electrosurgical procedure, the working fluid inside the electrode evaporates, filling the internal cavity with vapor. At the proximal end of the electrode, the vapor condenses, and the resulting liquid flows back toward the distal end of the device via a wick. Heat is thus carried away from the distal end to cool the electrode at the surgical site. At the proximal end of the electrode, a heat exchanger in the form of external heat conductive fins are used to carry heat away from the device. It should be noted that Levine's heat pipe assembly is one piece that requires complete immersion of the utensil in a sterilization system for cleaning, thus reducing it's working life.

In U.S. Pat. No. 5,908,418, issued to Dority et al., a hand held coagulating device is disclosed having a cooled handle for improved user comfort. An outer shell houses internal components of the device and provides a surface for the user to hold the device during a surgical procedure. A contact element positioned in an opening in a forward end of the shell is placed against an area of tissue to be coagulated, and radiation produced by a radiation source, such as an incandescent lamp, is transmitted through the contact element to the tissue. A heat sink is positioned in an opening in an aft end of the shell for conducting heat to the surrounding environment. A heat pipe is connected between the radiation source and the heat sink so that heat is transferred directly from the radiation source to the outside air while the surface used for holding the device remains cool.

There has been a long felt need for an improved cautery tool having a more efficiently designed and effective heat pipe cooling system.

SUMMARY OF THE INVENTION

The present invention provides a cautery surgical device comprising a surgical forceps including a pair of elongate arms each including a free end supporting an electrode tip for applying electrical energy to tissue. The arms of the surgical forceps are joined at another end so as to provide for resilient compressible movement of the arms between a normally open position, wherein the arms are disposed in aligned, substantially parallel, spaced-apart relation and a squeezed closed position, wherein the electrode tips are disposed in abutting relationship. The arms of the surgical forceps further include respective spaced-apart free ends and a receptacle extending along each arm from the free end toward the joined end. A heat pipe is releasably mounted to each arm for conducting heat away from the electrode tip. Each heat pipe comprises an evaporator portion having an end and a first diameter, with the electrode tip mounted to the evaporator end. A condenser portion of the heat pipe is spaced away from the evaporator end, and advantageously transitions from the first diameter to at least one smaller diameter section. In a preferred embodiment of the invention, the heat pipe further includes a cylindrical tube having an evaporation end, a condensation end, and a central passageway that is lined with a wick and at least partially filled with a fluid. The condensation end comprises a diameter that is smaller than the diameter of the evaporation end so as to be releasably received within a socket disposed within the receptacle of each arm. The socket includes a longitudinal blind hole that is sized so as to releasably receive the smaller diameter section of the condenser portion and means for releasably engaging a portion of the arm.

BRIEF DESCRIPTION OF THE DRAWINGS

These and other features and advantages of the present invention will be more fully disclosed in, or rendered obvious by, the following detailed description of the preferred embodiment of the invention, which is to be considered together with the accompanying drawings wherein like numbers refer to like parts and further wherein.

DETAILED DESCRIPTION OF THE PREFERRED EMBODIMENTS

This description of preferred embodiments is intended to be read in connection with the accompanying drawings, which are to be considered part of the entire written description of this invention. The drawing figures are not necessarily to scale and certain features of the invention may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "Inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. The term "operatively connected" is such an attachment, coupling or connection that allows the pertinent structures to operate as intended by virtue of that relationship. In the claims, means-plus-function clauses are intended to cover the structures described, suggested, or rendered obvious by the written description or drawings for performing the recited function, including not only structural equivalents but also equivalent structures.

Figure 1:
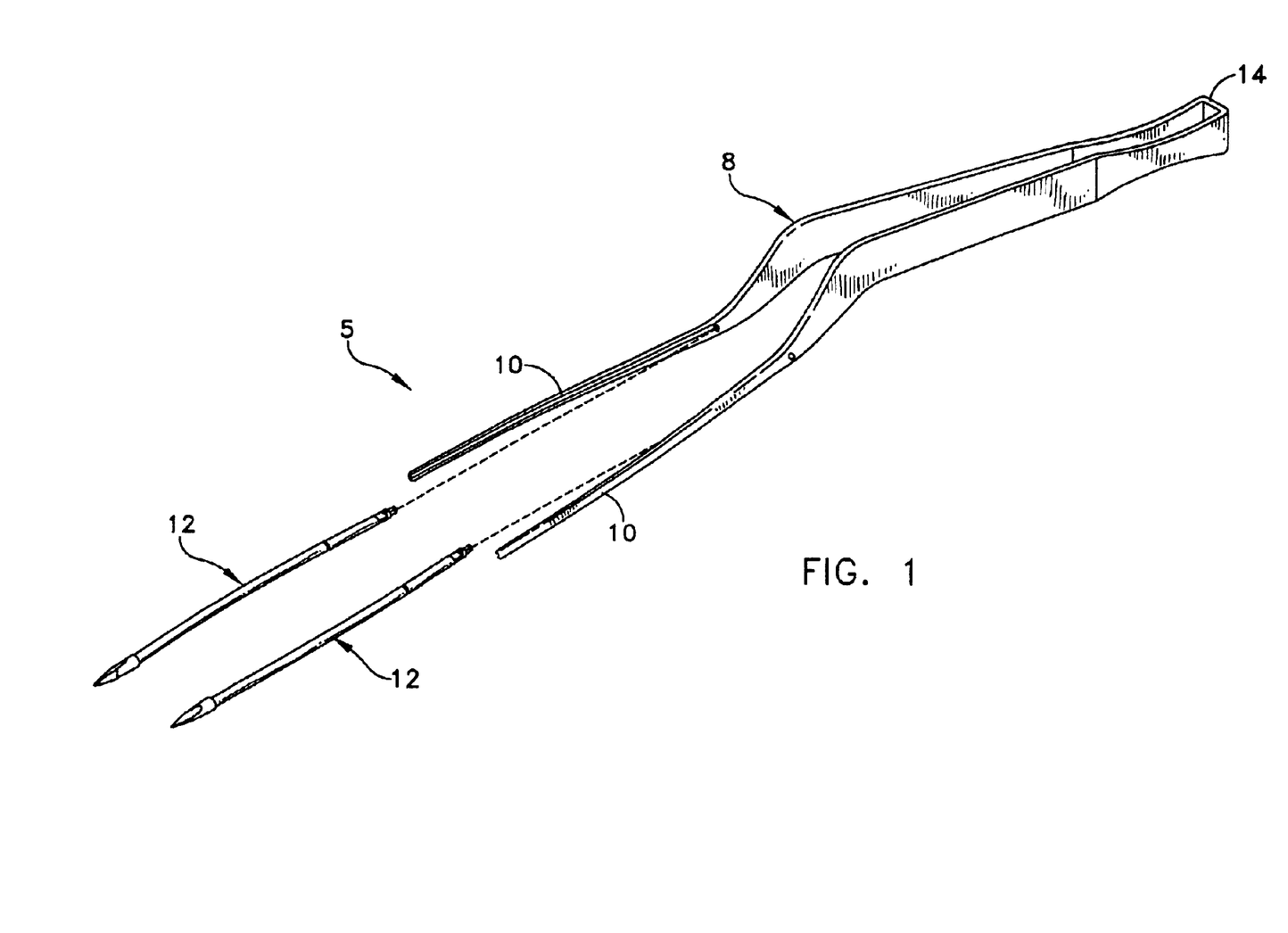
FIG. 1 is an exploded perspective view of a heat pipe cooled cautery surgical instrument formed in accordance with the present invention.
Figures 2, 3:
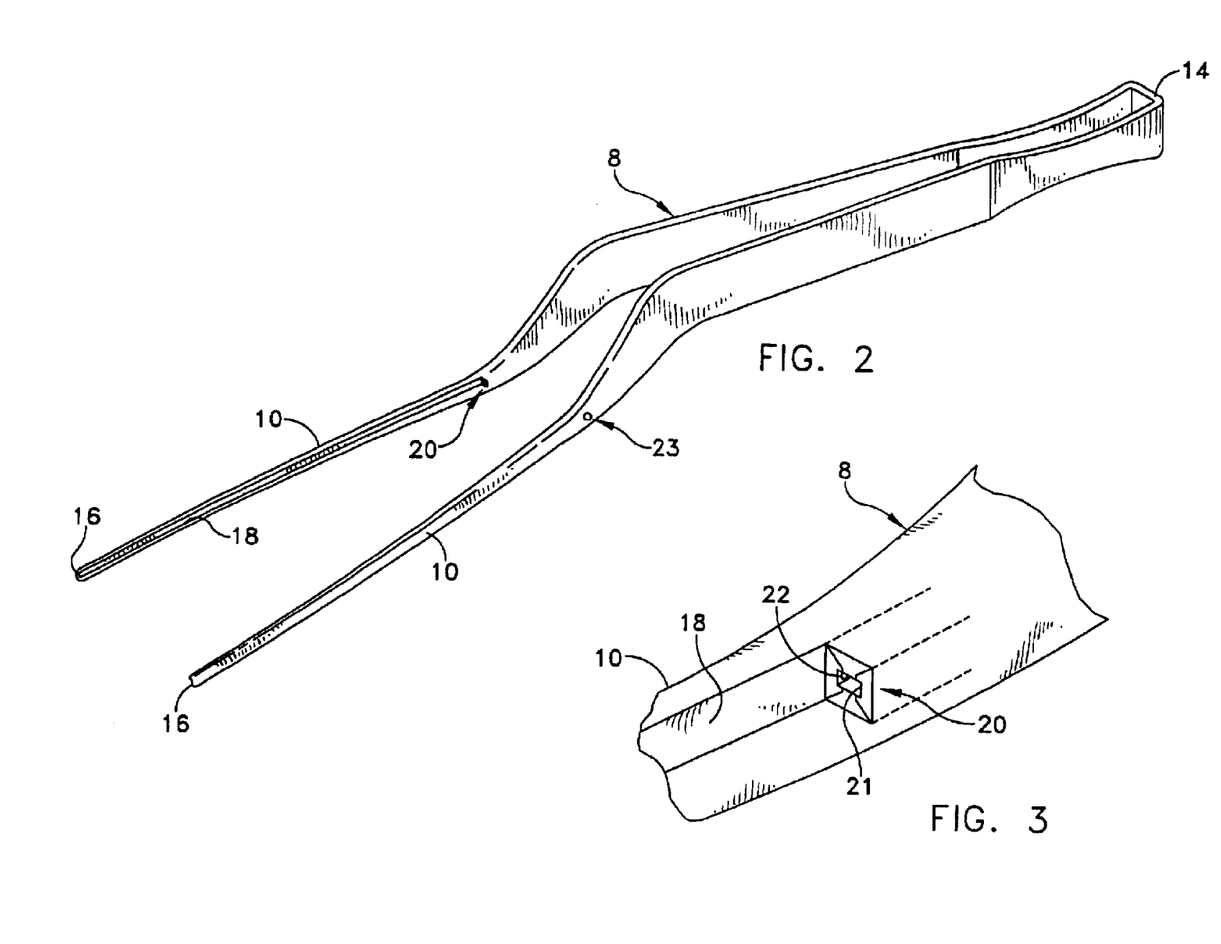
FIG. 2 is a perspective view of the surgical instrument shown in FIG. 1, but with the mandibles removed for clarity of illustration.
FIG. 3 is a broken away, perspective view of a portion of the surgical instrument shown in FIGS. 1 and 2, showing a groove and receptacle socket formed in accordance with the present invention.

Referring to FIGS. 1 and 2, a heat pipe cooled cautery system 5 formed in accordance with the present invention comprises an electrosurgical device in the form of a forceps 8 including a pair of outwardly biased arms 10 and a pair of mandible assemblies 12. More particularly, arms 10 are often formed from a titanium alloy, and are fastened to one another at a grip end 14 in a conventional way. Each arm 10 has a free end 16 (FIG. 2). In this construction, when arms 10 are squeezed or pinched together at their free ends 16, they tend to spring apart from one another upon release of the pinching pressure. Each arm 10 includes a groove 18 that is formed on an interior wall of arm 10 so that grooves 18 are in substantially confronting relation to one another. A receptacle socket 20 is formed at the end of each groove 18 so as to be located between grip end 14 and free end 16 (FIGS. 2 and 3). Receptacle socket 20 comprises a slot 21 and a conventional release mechanism 22 that protrudes into receptacle socket 20. A release button 23 protrudes outwardly from the outer surface of each arm 10, and is operatively connected to release mechanism 22 in a conventional manner. Of course, receptacle socket 20 may also be formed within a tubular arm 10 without departing from the scope of the present invention.

A bipolar generator (not shown) of the type well known in the art for providing radio frequency (RF) output that is suitable for surgical procedures is interconnected to arms 10 in a conventional manner. One bipolar generator suitable for use with the present invention is a CMC III bipolar generator, manufactured by Valley Forge Scientific Corp., Oaks, Pa., and described in U.S. Pat. No. 5,318,563 which patent is incorporated herein by reference. In a typical application, electrical current is applied to preselected tissue using a portion of mandible assembly 12 as a unipolar electrode.

During surgery, a return electrode is attached to the patient at a position away from the surgical site. The bipolar generator is then used to energize the electrode. The exposed end of the electrode is brought into contact with preselected tissue of a patient which results in a current path being provided between the electrode and the patient. RF current from the electrode develops a high temperature region about the electrode's exposed end which destroys the selected tissue. In order to regulate the temperature at the surgical site, mandible assemblies 12 comprise a heat pipe 25, a socket 28, and an electrode tip 30 (FIGS. 4–9).

More particularly, heat pipe 25 comprises a vacuum tight tube 32, a wick 35, and a working fluid 37 (FIGS. 7–10). Tube 32 is often a relatively long cylinder formed from a highly thermally conductive material, e.g., copper, aluminum, or their alloys, monel, or the like. A vapor space 43 (FIG. 10) is defined by a central passageway extending along the longitudinal axis of vacuum tight tube 32. Heat pipe 25 may include a conductive outer sleeve that is covered with an insulating cover which may extend along its length.

Figure 4:
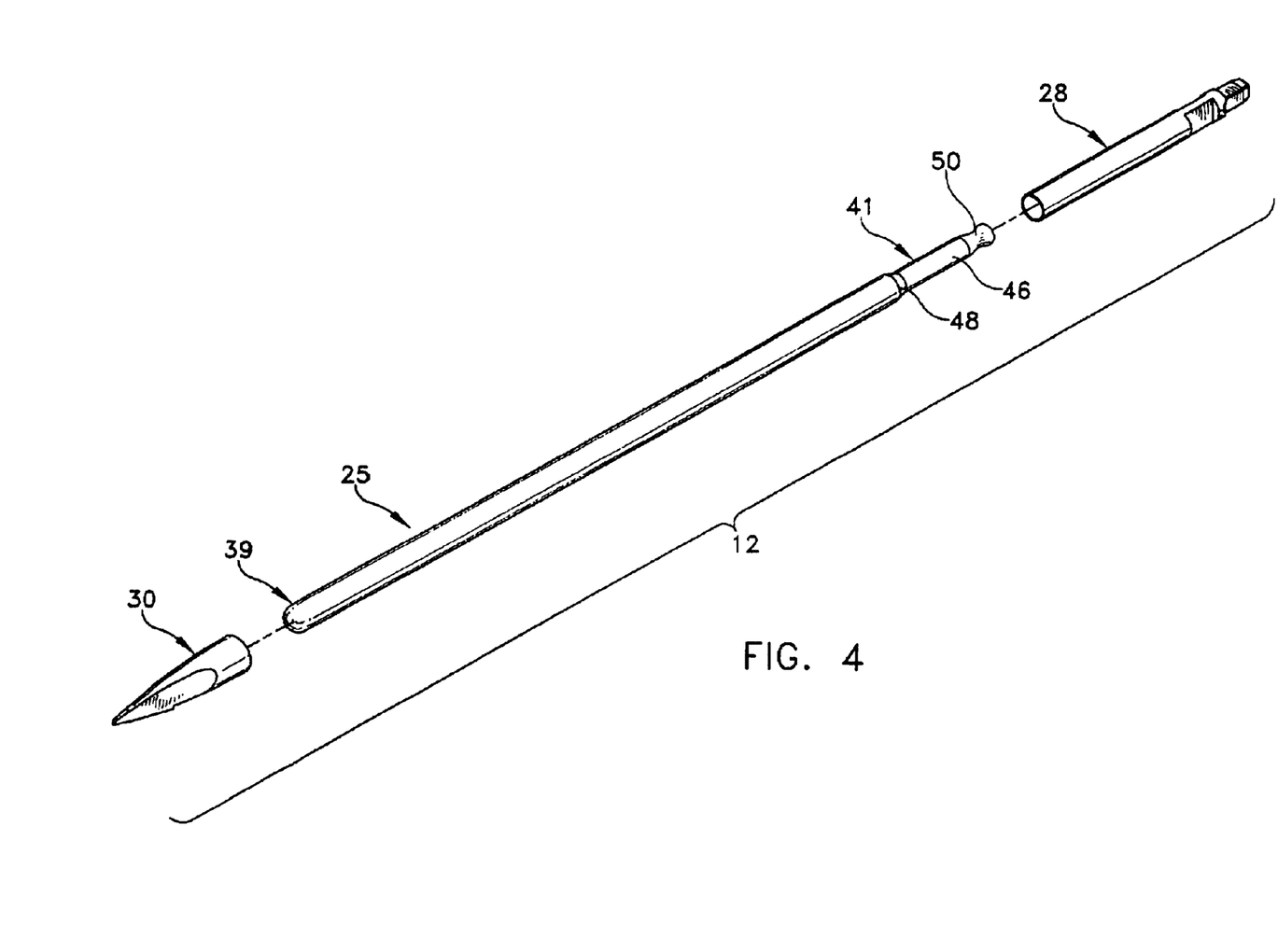
FIG. 4 is an exploded, perspective view of a mandible assembly formed in accordance with the present invention.
Figure 5:
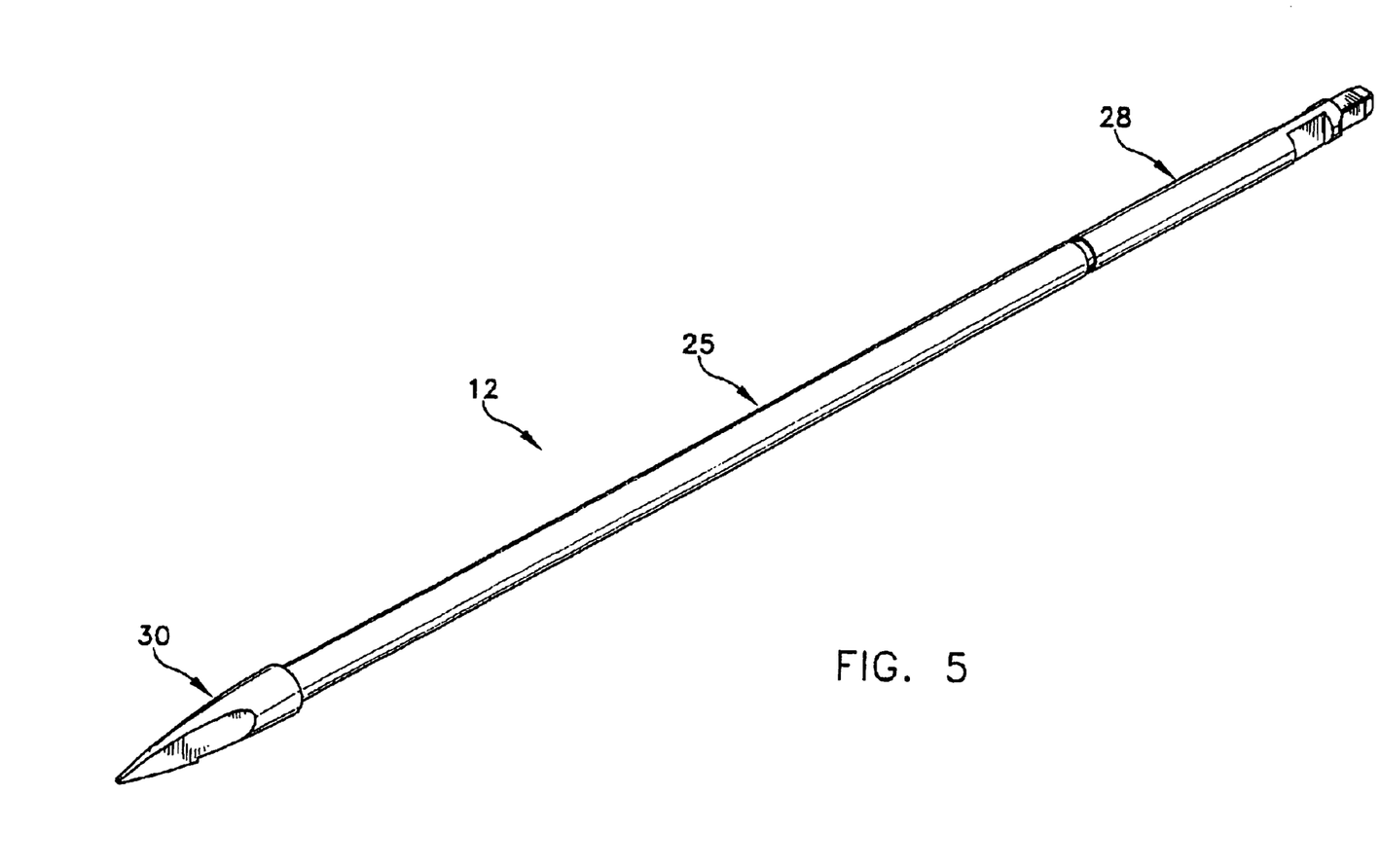
FIG. 5 is a perspective view of the mandible assembly shown in FIG. 4, fully assembled.
Figure 6:
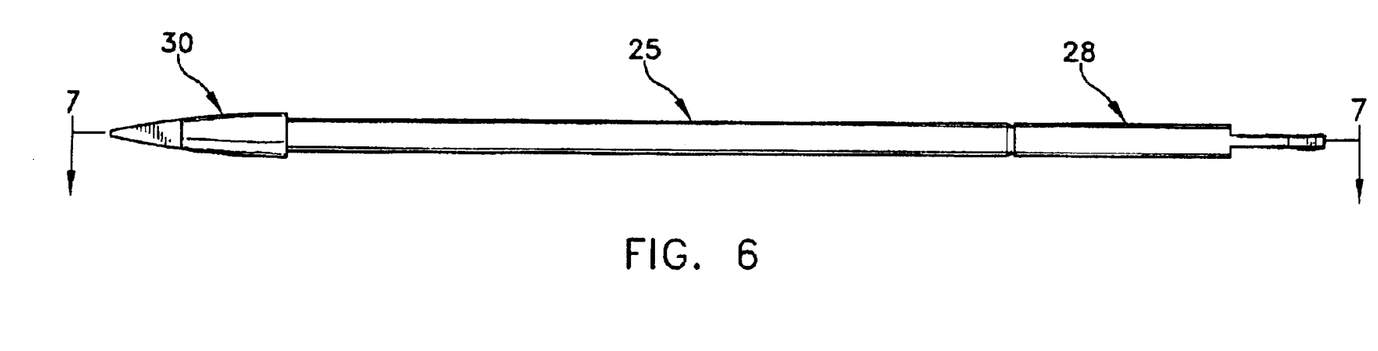
FIG. 6 is an elevational view of the mandible assembly shown in FIG. 5.
Figure 7:
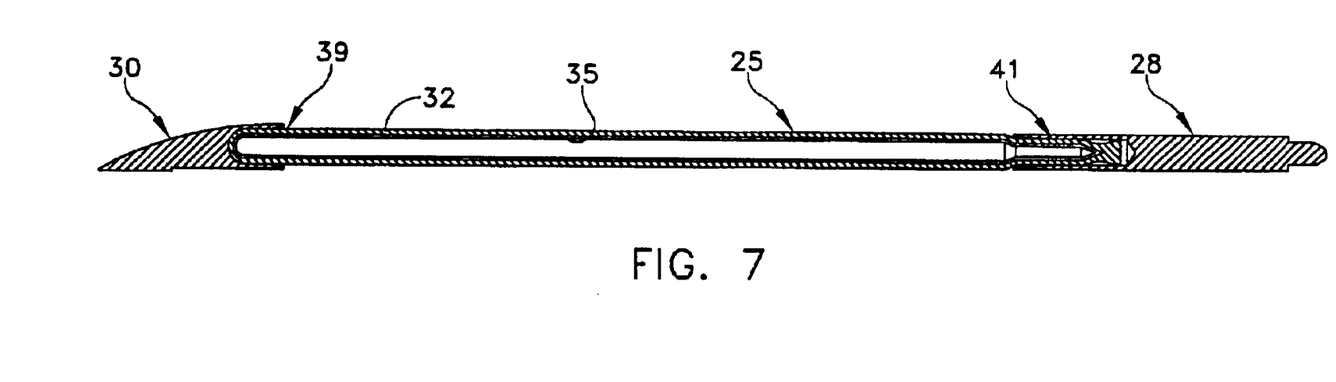
FIG. 7 is a cross-sectional view of the mandible assembly shown in FIG. 6, as taken along lines 7—7 in FIG. 6.
Figure 9:
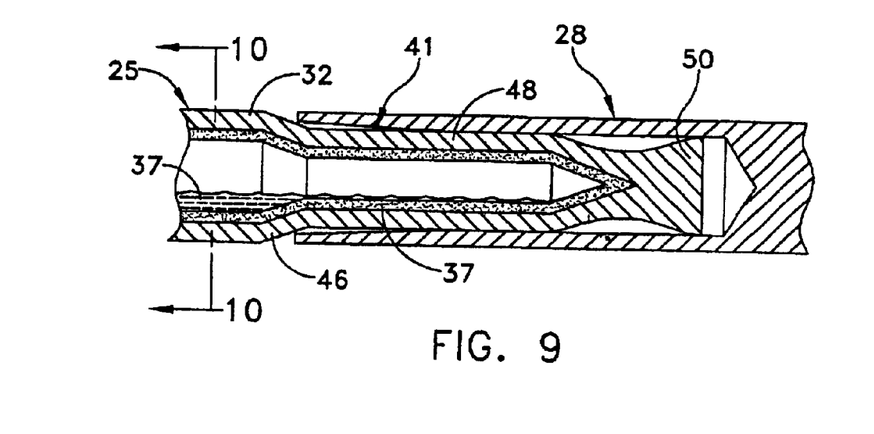
FIG. 9 is a broken away, enlarged cross-sectional view of a condenser portion of the mandible assembly shown in FIG. 7.
Figure 10:
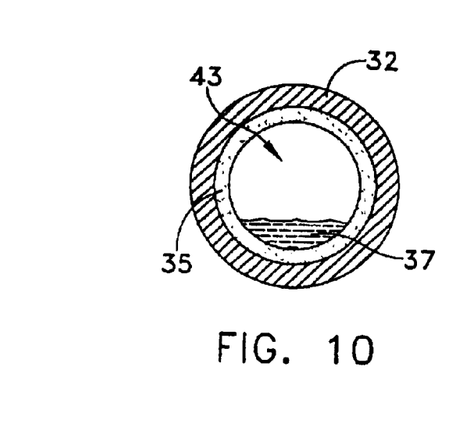
FIG. 10 is a cross-sectional view of the condenser portion of the mandible assembly shown in FIG. 9, as taken along lines 10—10 in FIG. 9.

Tube 32 comprises a substantially cylindrical evaporation end 39 and a condensation end 41 that has been formed so as to be at a decreased diameter. In a preferred embodiment, condensation end 41 is swaged (i.e., plastically deformed by a tool having a working surface profile that is complementary to the shape desired for the piece being plastically deformed) so that it includes a frusto-conical transition 46 that leads to a substantially cylindrical socket interface section 48 (FIGS. 4, 7, and 9). A seal 50 is formed at the distal end of heat pipe 25 adjacent to socket interface section 48. Seal 50 may comprise a pinched portion of tube 32, a further swaging of the distal end of condensation end 41, or a weld.

Wick 35 may comprise adjacent layers of screening or a sintered powder structure with interstices between the particles of powder. In one embodiment, wick 35 may comprise aluminum-silicon-carbide (AlSiC) or copper-silicon-carbide (CuSiC) having an average thickness of about 0.1 mm to 1.0 mm. Working fluid 37 may comprise any of the well known two-phase vaporizable liquids, e.g., water, alcohol, freon, etc. Heat pipe 25 is formed according to the invention by drawing a partial vacuum within tube 32, and then backfilling with a small quantity of working fluid 37, e.g., just enough to saturate wick 35 just prior to final hermetic sealing of tube 32 by pinching and welding or otherwise hermetically sealing off both ends. The atmosphere inside heat pipe 25 is set by an equilibrium of liquid and vapor.

Figure 11:
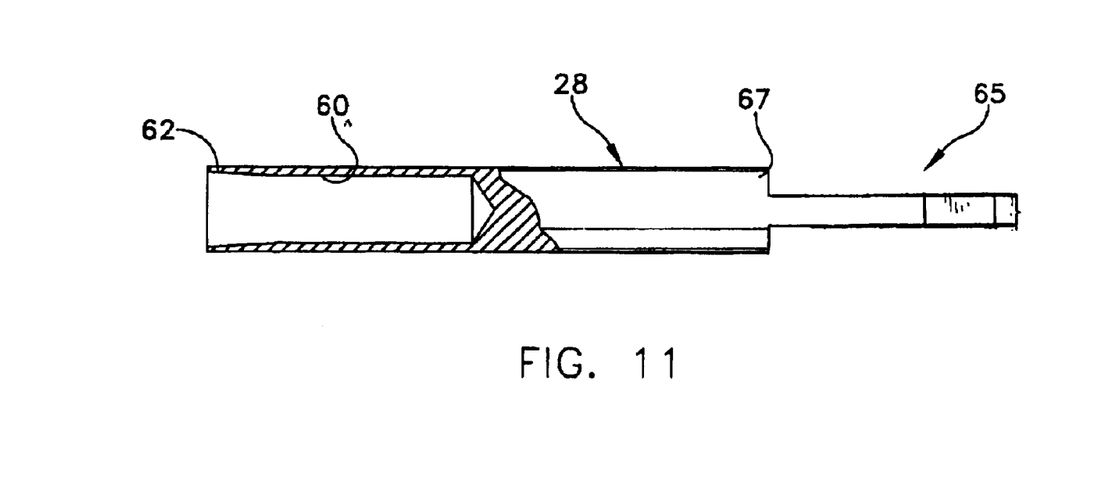
FIG. 11 is a side elevational view, partially in cross-section, of a socket formed in accordance with the present invention.
Figure 12:
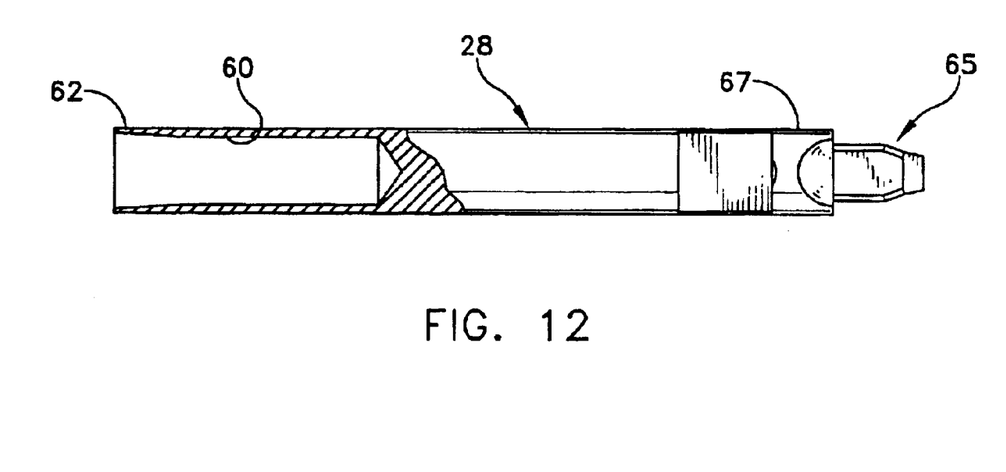
FIG. 12 is a side elevational view, partially in cross-section, of the socket shown in FIG. 11, rotated approximately 90° about its longitudinal axis.
Figure 13:
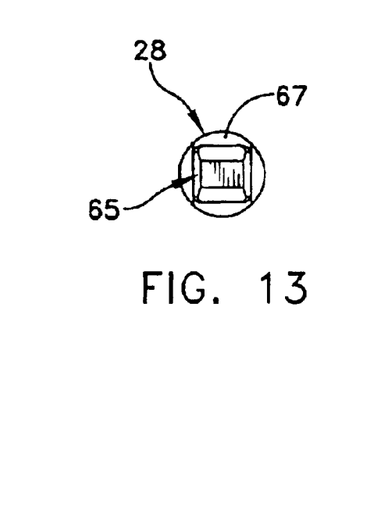
FIG. 13 is an end on view of the socket shown in FIGS. 11 and 12.

Referring to FIGS. 11–13, socket 28 may comprise either a thermally conductive cylindrical rod, e.g., a metal, or a less thermally conductive polymer of the type often used in medical devices. Socket 20 has a longitudinally oriented blind hole 60 at a first end 62, and a catch 65 positioned on a second end 67. The majority of heat pipe 25, i.e., all of evaporation end 39 up to, but not including condensation end 41, has substantially the same outer diameter as socket 28. Blind hole 60 is sized and shaped so as to releaseably receive condensation end 41 of heat pipe 25, i.e., blind hole 60 comprises a diameter that is only slightly larger than the outer diameter of cylindrical socket interface section 48, but slightly smaller than a portion of frusto-conical transition 46 (FIG. 9). Second end 67 of socket 28 is substantially solid with catch 65 projecting longitudinally outwardly from the terminal end of socket 28.

Figure 8:
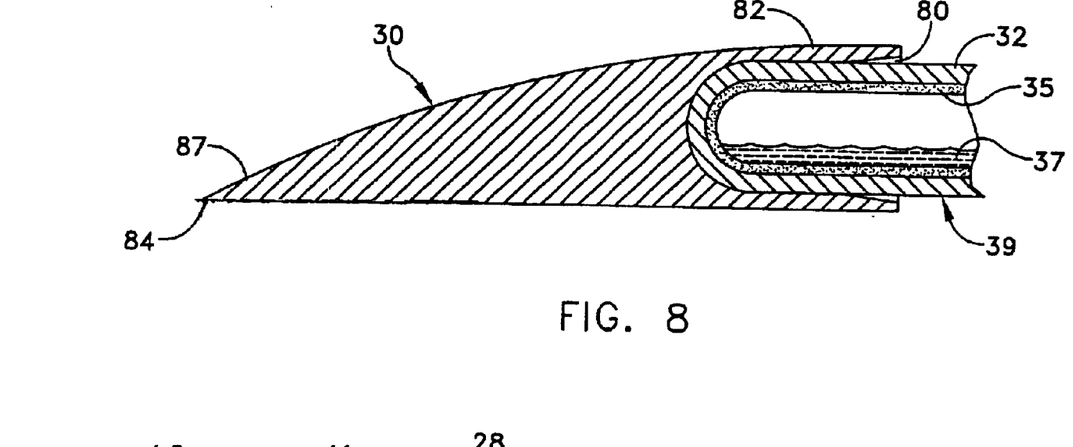
FIG. 8 is a broken away, enlarged cross—sectional view of an electrode tip and evaporator portion of the mandible assembly shown in FIG. 7.

Referring to FIG. 8, electrode tip 30 comprises a thermally and electrically conductive cap having a longitudinally oriented blind hole 80 at a first end 82, and a pointed tip 84. Blind hole 80 is sized and shaped so as to securely retain the tip portion of evaporation end 39 of heat pipe 25, i.e., blind hole 80 comprises a diameter that is only slightly larger than the outer diameter of evaporation end 39.

Each mandible assembly 12 is assembled by first positioning an electrode tip 30 on evaporator end 39 of tube 32. More particularly, electrode tip 30 is arranged so that blind hole 80 at first end 82 is positioned in coaxially aligned confronting relation to evaporator end 39 of tube 32. Once in this position, electrode tip 30 is moved toward tube 32 so that a portion of evaporator end 39 enters blind hole 80. It would be understood that blind hole 80 may include an appropriate thermal epoxy or a low temperature melting metal, e.g., solder, for maintaining electrode tip 30 in position on heat pipe 25. Alternatively, evaporation end 39 of heat pipe 25 may be formed so as to comprise the same profile as electrode tip 30.

Each heat pipe 25 may be assembled to forceps 8 in the following manner. A heat pipe 25 is first oriented so that cylindrical socket interface section 48 is positioned in confronting coaxial relation with blind hole 60 at first end 62 of a socket 28. Once in this position, heat pipe 25 is moved toward socket 28 so that seal 50, at the distal end of heat pipe 25, enters blind hole 60 of socket 28. Heat pipe 25 continues into socket 28 until fully received within blind hole 60. Heat pipe 25 is fixedly engaged within blind hole 60 by epoxy, brazing, or solder so as to form a mandible assembly 12.

Each mandible assembly 12 is then assembled to each arm 10 of forceps 8 by positioning catch 65 in aligned coaxial relation with groove 18 of arm 10. Once in this position, socket 28 is moved along groove 18 until it is received within receptacle socket 20 adjacent to the interior side of grip end 14 (FIG. 1). Once catch 65 has fully entered receptacle socket 20, release mechanism 22 is releasably engaged so as to hold socket 28 within arm 10.

In operation, electrode tip 30 is placed adjacent to tissue being treated. At the same time, the patient is maintained in contact with a grounding pad. RF electrical energy is applied to the tissue according to the desired tissue treatment, i.e., applied across electrode tips 30 and the grounding pad to treat the tissue. Heat pipe 25 serves to transfer heat away from electrode tip 30 during operation of cautery system 5. During operation, evaporation end electrode 39 is heated by the tissue. In accordance with the well-known operation of heat pipes, thermal energy is transferred through tube 32 to working fluid 37 residing in and on wick 35. Working fluid 35 evaporates, with the thus formed vapor traveling along the interior of heat pipe 25 from evaporation end 39 to condensation end 41. The vapor condenses in and around condensation end 41, and the resulting liquid flows back to evaporation end 39 via capillary action within wick 35. Heat is thus carried away from electrode tip 30. When the procedure is complete, each heat pipe 25 is removed from forceps 8 by merely depressing release button 23 on each arm 10 and pulling socket 28 from receptacle socket 20.

It is to be understood that the present invention is by no means limited only to the particular constructions herein disclosed and shown in the drawings, but also comprises any modifications or equivalents within the scope of the claims.

What is claimed is:

1. A heat pipe for use in a cautery surgical instrument comprising: a cylindrical tube having an evaporation end, a condensation end, and a central passageway that is lined with a wick and at least partially filled with a fluid wherein said condensation end comprises a diameter that is smaller than a diameter of said evaporation end; and further comprising an electrode tip fixedly mounted to said evaporation end, wherein said electrode tip comprises a thermally and electrically conductive cap having a longitudinally oriented blind hole at a first end, a pointed tip, and a tissue-engagement surface positioned on a second end.

2. A heat pipe according to claim 1 wherein said condensation end comprises at least one swaged portion.

3. A heat pipe according to claim 1 wherein said condensation end includes a frusto-conical transition portion that leads to a substantially cylindrical portion having a seal.

4. A heat pipe according to claim 3 wherein said seal comprises a swaged portion of said cylindrical tube.

5. A heat pipe according to claim 3 wherein said seal comprises at least one of a pinched portion and a welded portion of said cylindrical tube.

6. A heat pipe according to claim 1 wherein said blind hole comprises a diameter that is only slightly larger than an outer diameter of said evaporation end.

7. A heat pipe according to claim 6 wherein said evaporation end is secured within said blind hole by at least one of epoxy and solder.

* * * * *